United States Patent [19]

Kirino et al.

[11] Patent Number: 4,484,942
[45] Date of Patent: Nov. 27, 1984

[54] N-BENZYLPHENYLACETAMIDE DERIVATIVES, AND THEIR PRODUCTION AND USE AS HERBICIDES

[75] Inventors: Osamu Kirino, Hyogo; Shunichi Hashimoto, Osaka; Hiroshi Matsumoto, Osaka; Hiromichi Oshio, Osaka, all of Japan

[73] Assignee: Sumitomo Chemical Company, Limited, Osaka, Japan

[21] Appl. No.: 518,771

[22] Filed: Aug. 2, 1983

Related U.S. Application Data

[63] Continuation of Ser. No. 226,863, Jan. 21, 1981, abandoned.

[30] Foreign Application Priority Data

Jan. 28, 1980 [JP] Japan ................... 55-9199

[51] Int. Cl.³ ................... A01N 9/20; C07C 103/76
[52] U.S. Cl. ................... 71/118; 564/166; 564/170; 564/182
[58] Field of Search ................... 564/166, 170, 182; 71/118

[56] References Cited

U.S. PATENT DOCUMENTS

| | | | |
|---|---|---|---|
| 3,586,713 | 6/1971 | Buu-Hoi et al. | 564/170 X |
| 3,706,796 | 12/1972 | Blake | 564/182 X |
| 3,732,253 | 5/1973 | Cavalleri et al. | 564/166 X |
| 4,246,198 | 1/1981 | Rosenberger et al. | 564/170 X |
| 4,274,862 | 6/1981 | Kirino et al. | 564/212 X |
| 4,288,244 | 9/1981 | Kirino et al. | 564/212 X |

FOREIGN PATENT DOCUMENTS 525651 5/1956 Canada ................... 564/170

OTHER PUBLICATIONS

Boltze et al., CA 59:5074h, (1963).
Pirdzhenov et al., CA 77:139759n, (1972).
Khaletskii et al., CA 58:1392h, (1962).

*Primary Examiner*—Thomas A. Waltz
*Attorney, Agent, or Firm*—Birch, Stewart, Kolasch & Birch

[57] ABSTRACT

A compound of the formula:

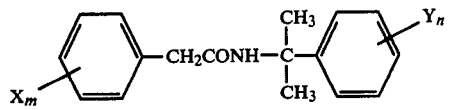

wherein X and Y, which may be same or different, are each a $C_1$–$C_3$ alkyl group, a halogen atom, a trifluoromethyl group, a nitro group or a $C_1$–$C_3$ alkoxy group, m is an integer of 0 to 3 and n is an integer of 1 or 2, which is useful as a herbicide.

13 Claims, No Drawings

N-BENZYLPHENYLACETAMIDE DERIVATIVES, AND THEIR PRODUCTION AND USE AS HERBICIDES

This application is a continuation of application Ser. No. 226,863 filed on Jan. 21, 1981; and now abandoned.

The present invention relates to N-benzylphenylacetamide derivatives, and their production and use.

The said N-benzylphenylacetamide derivatives are representable by the formula:

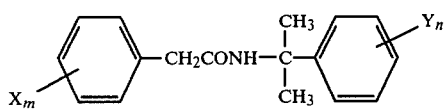

wherein X and Y, which may be same or different, are each a $C_1$–$C_3$ alkyl group, a halogen atom, a trifluoromethyl group, a nitro group or a $C_1$–$C_3$ alkoxy group, m is an integer of 0 to 3 and n is an integer of 1 or 2. In the above meanings, "halogen" includes fluorine, chlorine, bromine or iodine.

Among them, preferred are those of the formula (I) wherein X is methyl, fluorine, chlorine, trifluoromethyl or methoxy, m is an integer of 0 to 2, Y is methyl, fluorine, chlorine, bromine or methoxy and n is an integer of 1 or 2. Particularly preferred are those of the formula (I) wherein X is methyl, fluorine, chlorine or methoxy, m is an integer of 0 or 1, Y is methyl, fluorine or chlorine and n is an integer of 1, provided that when m or n is an integer of 1, X or Y is present at the m- or o-position on the benzene ring.

It has been found that the N-benzylphenylacetamide derivatives (I) are highly effective in preventing and exterminating farmland annual weeds such as *Echinochloa utilis*, large crabgrass (*Digitaria sanguinalis*), redroot pigweed (*Amaranthus retroflexus*), common purslane (*Portulaca oleracea*) and common lambsquarters (*Chenopodium album*) and paddy field annual weeds such as barnyard grass (*Echinochloa crus-galli*), pickerel weed (*Monochoria vaginalis*), false pimpernel (*Lindernia pyxidaria*) and *Dopatrium junceum*. It has also been found that the N-benzylphenylacetamide derivatives (I) exhibit a strong herbicidal activity against paddy field perennial weeds such as *Cyperus serotinus, Sagittaria pygmaea, Scirpus Hotarui*, slender spikerush (*Eleocharis aciculalis*) and *Eleocharis kuroguwai* as well as paddy field annual weeds as noted above and show a very broad herbicidal spectrum. Moreover, it may be noted that, while the prevention and extermination of perennial weeds such as purple nutsedge (*Cyperus rotundus*) in farmland are generally difficult, the N-benzylphenylacetamide derivatives (I) exert a strong herbicidal activity against it by pre-emergence treatment or post-emergence treatment.

Advantageously, the N-benzylphenylacetamide derivatives (I) produce a strong herbicidal potency on the application to farmland, particularly by soil surface treatment or soil mixing treatment prior to emergence of weeds, without causing any harmful effect on various crop plants (e.g. rice, soybean, cotton, corn, peanut, sugarbeet, sunflower) and vegetables (e.g. lettuce, cabbage).

Accordingly, the N-benzylphenylacetamide derivatives (I) are useful as herbicides applicable for paddy field and farmland. They are also useful as herbicides to be employed for vegetable garden, orchard, lawn, pasture, tea garden, mulberry field, rubber plantation, forest, nonagricultural land, etc.

U.S. Pat. No. 3,498,781 discloses some pivalic acid amide derivatives, which are somewhat similar to the N-benzylphenylacetamide derivatives (I) in chemical structure and have a herbicidal activity. However, the herbicidal activity of the N-benzylphenylacetamide derivatives (I) is generally more excellent than that of the pivalic acid amide derivatives. It is particularly notable that, in comparison with the pivalic acid amide derivatives, the N-benzylphenylacetamide derivatives (I) exert an extremely high herbicidal effect on perennial field weeds such as nutsedge sp. (e.g. *Cyperus rotundus*) and Gramineae weeds without any phytotoxicity to soybean, cotton, corn, rice plants or sugarbeet.

The N-benzylphenylacetamide derivatives (I) can be produced by reacting a phenylacetic acid or its reactive derivative of the formula:

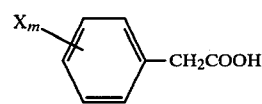

wherein X and m are each as defined above with a benzylamine derivative of the formula:

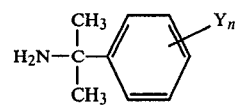

wherein Y and n are each as defined above.

The benzylamine derivative (III) is obtainable, for instance, by the method as disclosed in J.Am.Chem.Soc., 71, 3929 (1949).

For the reaction, the phenylacetic acid or its reactive derivative (II) may be used in an amount of 0.4 to 1.5 equivalents, preferably of 0.5 to 1.1 equivalents to one equivalent of the benzylamine derivative (III). The reaction may be carried out in the presence or absence of an inert solvent. Examples of the inert solvent are hydrocarbons (e.g. benzene, toluene, xylene), halogenated hydrocarbons (e.g. chlorobenzene, methylene chloride, chloroform, carbon tetrachloride), ethers (e.g. diisopropyl ether, tetrahydrofuran, dioxane), alcohols (e.g. methanol, ethanol, isopropanol), ketones (e.g. acetone, methylethylketone, methylisobutylketone), esters (e.g. ethyl acetate), nitriles (e.g. acetonitrile), dimethylsulfoxide, dimethylformamide, water, etc. Among them, particularly preferred is benzene. The reaction can be effected within a wide range of temperature from the freezing temperature to the boiling temperature of the reaction mixture, preferably from 0° C. to the the boiling temperature of the reaction mixture. If necessary, cooling or heating may be adopted.

As the phenylacetic acid or its reactive derivative (II), there may be used carboxylic acid, acid anhydride, acid chloride, acid bromide, carboxylic acid ester, etc. Depending upon its kind, an appropriate reaction aid may be employed in the reaction. In case of the carboxylic acid, dicyclohexylcarbodiimide, phosphorus pentachloride, phosphorus trichloride, phosphorus tribromide, thionyl chloride, sodium hydroxide, potassium hydroxide, sodium ethoxide, sodium methoxide, triethylamine, pyridine, quinoline, isoquinoline, N,N-dimethylaniline, N,N-diethylaniline, N-methylmorpholine, etc. are usable as the reaction aid. In case of the acid chloride or acid bromide, sodium hydroxide, potassium hydroxide, sodium ethoxide, sodium methoxide, triethylamine, pyridine, quinoline, isoquinoline, N,N-dimethylaniline, N,N-diethylaniline, N-methylmorpholine, sodium acetate, etc., preferably triethylamine, are usable as the reaction aid. When the reaction aid is employed, its amount may be from a catalytic amount to 1.5 equivalents, preferably from 0.95 to 1.1 equivalent to one equivalent of the material to be eliminated from the starting compounds as the result of the reaction.

The recovery of the reaction product from the reaction mixture may be carried out in a per se conventional manner. For instance, the reaction mixture is filtered and/or washed with water, followed by distillation for removal of the solvent to give the reaction product, i.e. the N-benzylphenylacetamide derivative (I). If desired, this reaction product may be purified by a per se conventional procedure such as recrystallization from an appropriate solvent such as benzene, toluene, methanol, ethanol or isopropyl ether.

Practical embodiments of the preparation of the N-benzylphenylacetamide derivatives (I) are illustratively shown in the following example.

EXAMPLE 1

Into a 300 ml four-necked flask, there were charged benzene (200 ml), 4-fluoro-α,α-dimethylbenzylamine (7.7 g) and triethylamine (6.0 g), and o-methylphenylacetyl chloride (9.5 g) was dropwise added thereto at room temperature while stirring, followed by refluxing for 3 hours. After cooling, the reaction mixture was washed with water to remove triethylamine hydrochloride. After the benzene layer was dried over anhydrous sodium sulfate, the solvent was distilled off under reduced pressure. The residue was recrystallized from ethanol to give 11.3 g of N-(4-fluoro-α,α-dimethylbenzyl)-o-methylphenylacetamide (Compound No. 11). M.P., 150°–151° C.

Elementary analysis ($C_{18}H_{20}NOF$): Calcd.: C, 75.76%; H, 7.06%; N, 4.91%. Found: C, 75.88%; H, 7.30%; N, 4.72%.

In the same manner as above, there are produced other N-benzylphenylacetamide derivatives (I), of which some specific examples are shown in Table 1.

TABLE 1

| Compound No. | Chemical structure | Melting point (°C.) | Elementary analysis (%) | | | |
|---|---|---|---|---|---|---|
| | | | | C | H | N | Halogen |
| 1 | Ph–CH$_2$CONH–C(CH$_3$)$_2$–(2-CH$_3$-C$_6$H$_4$) | 130–132 | Calcd. | 80.86 | 7.92 | 5.24 | — |
| | | | Found | 80.79 | 8.12 | 5.11 | — |
| 2 | Ph–CH$_2$CONH–C(CH$_3$)$_2$–(3-CH$_3$-C$_6$H$_4$) | 120.5–122 | Calcd. | 80.86 | 7.92 | 5.24 | — |
| | | | Found | 80.61 | 8.00 | 5.16 | — |
| 3. | Ph–CH$_2$CONH–C(CH$_3$)$_2$–(2,5-(CH$_3$)$_2$-C$_6$H$_3$) | 166–168 | Calcd. | 81.10 | 8.24 | 4.98 | — |
| | | | Found | 80.98 | 8.35 | 4.96 | — |
| 4 | Ph–CH$_2$CONH–C(CH$_3$)$_2$–(2-F-C$_6$H$_4$) | 141–143 | Calcd. | 75.25 | 6.69 | 5.16 | — |
| | | | Found | 75.29 | 6.80 | 5.18 | — |
| 5 | Ph–CH$_2$CONH–C(CH$_3$)$_2$–(4-F-C$_6$H$_4$) | 129.5–131 | Calcd. | 75.25 | 6.69 | 5.16 | — |
| | | | Found | 75.21 | 6.74 | 5.10 | — |
| 6 | Ph–CH$_2$CONH–C(CH$_3$)$_2$–(2-Cl-C$_6$H$_4$) | 114–115 | Calcd. | 70.95 | 6.30 | 4.87 | 12.32 (Cl) |
| | | | Found | 70.77 | 6.37 | 4.98 | 12.47 (Cl) |

TABLE 1-continued

| Compound No. | Chemical structure | Melting point (°C.) | Elementary analysis (%) | | | |
|---|---|---|---|---|---|---|
| | | | | C | H | N | Halogen |
| 7 | PhCH₂CONH–C(CH₃)₂–(2,4-diCl-C₆H₃) | 117.5-119 | Calcd. 63.37 5.32 4.35 22.00 (Cl) <br> Found 63.28 5.31 4.43 22.13 (Cl) | | | |
| 8 | PhCH₂CONH–C(CH₃)₂–(2,6-diCl-C₆H₃) | 151-152 | Calcd. 63.37 5.32 4.35 22.00 (Cl) <br> Found 63.28 5.35 4.39 21.98 (Cl) | | | |
| 9 | PhCH₂CONH–C(CH₃)₂–(3-Br-C₆H₄) | 117-119 | Calcd. 61.46 5.46 4.22 24.05 (Br) <br> Found 61.58 5.71 4.16 24.20 (Br) | | | |
| 10 | (2-CH₃-C₆H₄)CH₂CONH–C(CH₃)₂–(3-CH₃-C₆H₄) | 103-104 | Calcd. 81.10 8.24 4.98 — <br> Found 81.30 8.21 5.04 — | | | |
| 11 | (2-CH₃-C₆H₄)CH₂CONH–C(CH₃)₂–(4-F-C₆H₄) | 150-151 | Calcd. 75.76 7.06 4.91 — <br> Found 75.88 7.30 4.72 — | | | |
| 12 | (2-CH₃-C₆H₄)CH₂CONH–C(CH₃)₂–(2-Cl-C₆H₄) | 124-125 | Calcd. 71.63 6.68 4.64 11.75 (Cl) <br> Found 71.48 6.80 4.80 11.77 (Cl) | | | |
| 13 | (3-CH₃-C₆H₄)CH₂CONH–C(CH₃)₂–(3-CH₃-C₆H₄) | 96-98 | Calcd. 81.10 8.24 4.98 — <br> Found 81.32 8.30 4.77 — | | | |
| 14 | (3-CH₃-C₆H₄)CH₂CONH–C(CH₃)₂–(2-Cl-C₆H₄) | 98-99 | Calcd. 71.63 6.68 4.64 11.75 (Cl) <br> Found 71.71 6.79 4.62 11.77 (Cl) | | | |
| 15 | (4-CH₃-C₆H₄)CH₂CONH–C(CH₃)₂–(2-Cl-C₆H₄) | 109-110 | Calcd. 71.63 6.68 4.64 11.75 (Cl) <br> Found 71.80 6.54 4.89 11.68 (Cl) | | | |
| 16 | (2-iC₃H₇-C₆H₄)CH₂CONH–C(CH₃)₂–(3-F-C₆H₄) | 75-77 | Calcd. 76.65 7.72 4.47 — <br> Found 76.83 7.91 4.28 — | | | |

TABLE 1-continued

| Compound No. | Chemical structure | Melting point (°C.) | Elementary analysis (%) | | | | |
|---|---|---|---|---|---|---|---|
| | | | | C | H | N | Halogen |
| 17 | 2-F-C6H4-CH2CONH-C(CH3)2-(3-CH3-C6H4) | 112–113 | Calcd. | 75.76 | 7.06 | 4.91 | — |
| | | | Found | 75.69 | 7.23 | 4.88 | — |
| 18 | 2-F-C6H4-CH2CONH-C(CH3)2-(2-Cl-C6H4) | 119–120.5 | Calcd. | 66.78 | 5.60 | 4.58 | 11.59 (Cl) |
| | | | Found | 66.80 | 5.82 | 4.66 | 11.38 (Cl) |
| 19 | 2-Cl-C6H4-CH2CONH-C(CH3)2-(3-CH3-C6H4) | 144–146 | Calcd. | 71.63 | 6.68 | 4.64 | 11.75 (Cl) |
| | | | Found | 71.82 | 6.71 | 4.50 | 11.63 (Cl) |
| 20 | 4-Cl-C6H4-CH2CONH-C(CH3)2-(2-Cl-C6H4) | 129–131 | Calcd. | 63.37 | 5.32 | 4.35 | 22.00 (Cl) |
| | | | Found | 63.61 | 5.49 | 4.65 | 22.14 (Cl) |
| 21 | 4-Br-C6H4-CH2CONH-C(CH3)2-(3-CH3-C6H4) | 110–112 | Calcd. | 62.44 | 5.82 | 4.05 | 23.08 (Br) |
| | | | Found | 62.62 | 5.90 | 3.89 | 23.19 (Br) |
| 22 | 3-F3C-C6H4-CH2CONH-C(CH3)2-(3-CH3-C6H4) | 79–82 | Calcd. | 68.05 | 6.01 | 4.18 | — |
| | | | Found | 67.92 | 5.88 | 4.32 | — |
| 23 | 4-O2N-C6H4-CH2CONH-C(CH3)2-(3-CH3-C6H4) | 204–207 | Calcd. | 69.21 | 6.45 | 8.97 | — |
| | | | Found | 69.18 | 6.22 | 9.16 | — |
| 24 | 2-OCH3-C6H4-CH2CONH-C(CH3)2-(3-CH3-C6H4) | 73–74.5 | Calcd. | 76.74 | 7.80 | 4.71 | — |
| | | | Found | 76.84 | 7.83 | 4.80 | — |
| 25 | 2-OCH3-C6H4-CH2CONH-C(CH3)2-(2,5-di-CH3-C6H3) | 156–157 | Calcd. | 77.14 | 8.09 | 4.50 | — |
| | | | Found | 76.99 | 8.15 | 4.63 | — |
| 26 | 2-OCH3-C6H4-CH2CONH-C(CH3)2-(2-Cl-C6H4) | 79.5–81.5 | Calcd. | 68.03 | 6.34 | 4.41 | 11.16 (Cl) |
| | | | Found | 68.33 | 6.24 | 4.47 | 10.94 (Cl) |

TABLE 1-continued

| Compound No. | Chemical structure | Melting point (°C.) | Elementary analysis (%) | | | |
|---|---|---|---|---|---|---|
| | | | | C | H | N | Halogen |
| 27 | CH3O-C6H4-CH2CONH-C(CH3)2-C6H4-Cl (3-OMe, 2-Cl) | 96–97 | Calcd.<br>Found | 68.03<br>67.85 | 6.34<br>6.31 | 4.41<br>4.52 | 11.16 (Cl)<br>11.38 (Cl) |
| 28 | C2H5O-C6H4-CH2CONH-C(CH3)2-C6H4-CH3 | 98–100 | Calcd.<br>Found | 77.14<br>77.02 | 8.09<br>8.25 | 4.50<br>4.33 | —<br>— |
| 29 | (CH3O)3-C6H2-CH2CONH-C(CH3)2-C6H4-Cl | 118.5–120 | Calcd.<br>Found | 63.57<br>63.41 | 6.40<br>6.59 | 3.71<br>3.80 | 9.38 (Cl)<br>9.58 (Cl) |
| 30 | CH3-C6H4-CH2CONH-C(CH3)2-C6H4-CH3 | 127–128.5 | Calcd.<br>Found | 81.10<br>81.23 | 8.24<br>8.19 | 4.98<br>4.93 | —<br>— |
| 31 | CH3-C6H4-CH2CONH-C(CH3)2-C6H4-Cl | 132–133.5 | Calcd.<br>Found | 71.63<br>71.81 | 6.68<br>6.89 | 4.64<br>4.62 | 11.75 (Cl)<br>11.82 (Cl) |
| 32 | F-C6H4-CH2CONH-C(CH3)2-C6H4-CH3 | 125.5–127 | Calcd.<br>Found | 75.76<br>75.87 | 7.06<br>7.18 | 4.91<br>4.89 | —<br>— |
| 33 | F-C6H4-CH2CONH-C(CH3)2-C6H4-Cl | 115–116 | Calcd.<br>Found | 66.78<br>66.68 | 5.60<br>5.70 | 4.58<br>4.54 | 11.59 (Cl)<br>11.68 (Cl) |
| 34 | Cl-C6H4-CH2CONH-C(CH3)2-C6H4-Cl | 125–126.5 | Calcd.<br>Found | 63.37<br>63.48 | 5.32<br>5.35 | 4.35<br>4.44 | 22.00 (Cl)<br>21.97 (Cl) |
| 35 | H3C-C6H4-CH2CONH-C(CH3)2-C6H4-Cl | 121–122.5 | Calcd.<br>Found | 71.63<br>71.81 | 6.68<br>6.78 | 4.64<br>4.61 | 11.75 (Cl)<br>11.65 (Cl) |
| 36 | C6H5-CH2CONH-C(CH3)2-C6H4-Cl | 109.5–110.5 | Calcd.<br>Found | 70.95<br>71.16 | 6.30<br>6.45 | 4.87<br>4.64 | 12.32 (Cl)<br>12.13 (Cl) |

TABLE 1-continued

| Compound No. | Chemical structure | Melting point (°C.) | | Elementary analysis (%) | | | |
|---|---|---|---|---|---|---|---|
| | | | | C | H | N | Halogen |
| 37 | C₆H₅-CH₂CONH-C(CH₃)₂-C₆H₄-CH₃ (p) | 132-133 | Calcd. Found | 80.86 80.78 | 7.92 8.06 | 5.24 5.18 | — — |
| 38 | C₆H₅-CH₂CONH-C(CH₃)₂-C₆H₄-C₂H₅ (p) | 117-119 | Calcd. Found | 81.10 80.95 | 8.24 8.35 | 4.98 4.86 | — — |
| 39 | C₆H₅-CH₂CONH-C(CH₃)₂-C₆H₄-Br (p) | 162-163 | Calcd. Found | 61.46 61.46 | 5.46 5.54 | 4.22 4.23 | 24.05 (Br) 23.98 (Br) |
| 40 | C₆H₅-CH₂CONH-C(CH₃)₂-C₆H₄-OCH₃ (p) | 110.5-112 | Calcd. Found | 76.30 76.11 | 7.47 7.26 | 4.94 4.82 | — — |
| 41 | (o-CH₃)C₆H₄-CH₂CONH-C(CH₃)₂-C₆H₄-F (m) | 150-151.5 | Calcd. Found | 75.76 75.78 | 7.06 7.18 | 4.91 4.82 | — — |
| 42 | (o-CH₃)C₆H₄-CH₂CONH-C(CH₃)₂-C₆H₄-CH₃ (p) | 155-156 | Calcd. Found | 81.10 81.07 | 8.24 8.43 | 4.98 4.99 | — — |
| 43 | (o-F)C₆H₄-CH₂CONH-C(CH₃)₂-C₆H₄-CH₃ (o) | 125.5-127 | Calcd. Found | 75.76 75.80 | 7.06 7.28 | 4.91 4.87 | — — |
| 44 | (o-F)C₆H₄-CH₂CONH-C(CH₃)₂-C₆H₄-CH₃ (p) | 135-136.5 | Calcd. Found | 75.76 75.89 | 7.06 7.23 | 4.91 4.95 | — — |
| 45 | (o-F)C₆H₄-CH₂CONH-C(CH₃)₂-C₆H₄-Br (p) | 178-179 | Calcd. Found | 58.30 58.27 | 4.89 4.90 | 4.00 3.96 | 22.81 (Br) 22.91 (Br) |
| 46 | (o-Cl)C₆H₄-CH₂CONH-C(CH₃)₂-C₆H₄-Cl (o) | 143-145 | Calcd. Found | 63.37 63.54 | 5.32 5.39 | 4.35 4.25 | 22.00 (Cl) 21.93 (Cl) |
| 47 | (o-Cl)C₆H₄-CH₂CONH-C(CH₃)₂-C₆H₄-CH₃ (p) | 94-95 | Calcd. Found | 71.63 71.72 | 6.68 6.84 | 4.64 4.60 | 11.75 (Cl) 11.95 (Cl) |

TABLE 1-continued

| Compound No. | Chemical structure | Melting point (°C.) | Elementary analysis (%) | | | |
|---|---|---|---|---|---|---|
| | | | | C | H | N | Halogen |
| 48 | 2-Cl-C6H4-CH2CONH-C(CH3)2-C6H4-4-CH3 | 134–136 | Calcd.<br>Found | 71.63<br>71.47 | 6.68<br>6.87 | 4.64<br>4.62 | 11.75 (Cl)<br>11.79 (Cl) |
| 49 | 2-OCH3-C6H4-CH2CONH-C(CH3)2-C6H4-2-CH3 | 112–113 | Calcd.<br>Found | 76.74<br>76.69 | 7.80<br>7.95 | 4.71<br>4.65 | —<br>— |
| 50 | 2-OCH3-C6H4-CH2CONH-C(CH3)2-C6H4-3-Cl | 95–96.5 | Calcd.<br>Found | 68.03<br>68.22 | 6.34<br>6.42 | 4.41<br>4.32 | 11.16 (Cl)<br>11.30 (Cl) |
| 51 | 2-OCH3-C6H4-CH2CONH-C(CH3)2-C6H4-4-CH3 | 111–113 | Calcd.<br>Found | 76.74<br>76.72 | 7.80<br>7.95 | 4.71<br>4.73 | —<br>— |
| 52 | 3-CH3-C6H4-CH2CONH-C(CH3)2-C6H4-2-CH3 | 110.5–111.5 | Calcd.<br>Found | 81.10<br>81.32 | 8.24<br>8.07 | 4.98<br>5.07 | —<br>— |
| 53 | 3-CH3-C6H4-CH2CONH-C(CH3)2-C6H4-4-CH3 | 123–124 | Calcd.<br>Found | 81.10<br>80.95 | 8.24<br>8.41 | 4.98<br>5.01 | —<br>— |
| 54 | 3-CH3-C6H4-CH2CONH-C(CH3)2-C6H4-4-F | 97–99 | Calcd.<br>Found | 75.76<br>75.76 | 7.06<br>7.19 | 4.91<br>4.80 | —<br>— |
| 55 | 3-Cl-C6H4-CH2CONH-C(CH3)2-C6H4-2-CH3 | 133–134 | Calcd.<br>Found | 71.63<br>71.72 | 6.68<br>6.70 | 4.64<br>4.60 | 11.75 (Cl)<br>11.78 (Cl) |
| 56 | 3-Cl-C6H4-CH2CONH-C(CH3)2-C6H4-2-Cl | 125–127 | Calcd.<br>Found | 63.37<br>63.24 | 5.32<br>5.41 | 4.35<br>4.32 | 22.00 (Cl)<br>21.91 (Cl) |
| 57 | 3-Cl-C6H4-CH2CONH-C(CH3)2-C6H4-3-CH3 | 105–106 | Calcd.<br>Found | 71.63<br>71.40 | 6.68<br>6.60 | 4.64<br>4.60 | 11.75 (Cl)<br>11.98 (Cl) |

TABLE 1-continued

| Compound No. | Chemical structure | Melting point (°C.) | Elementary analysis (%) | | | |
|---|---|---|---|---|---|---|
| | | | | C | H | N | Halogen |
| 58 | Cl-C6H4-CH2CONH-C(CH3)2-C6H4-Cl | 139–140 | Calcd. 63.37 5.32 4.35 22.00 (Cl)<br>Found 63.38 5.30 4.39 22.21 (Cl) |
| 59 | Cl-C6H4-CH2CONH-C(CH3)2-C6H4-CH3 | 135.5–136.5 | Calcd. 71.63 6.68 4.64 11.75 (Cl)<br>Found 71.48 6.84 4.56 11.85 (Cl) |
| 60 | Cl-C6H4-CH2CONH-C(CH3)2-C6H4-Br | 160–161 | Calcd. 55.68 4.67 3.82 21.79 (Br), 9.67 (Cl)<br>Found 55.74 4.71 3.87 21.88 (Br), 9.50 (Cl) |

In the practical usage of the N-benzylphenylacetamide derivatives (I), they may be applied as such or in any preparation form such as granules, fine granules, dusts, coarse dusts, wettable powders, emulsifiable concentrates or oily suspensions.

For production of said preparation forms, solid or liquid carriers or diluents may be used. As for the solid carrier or diluent, there may be exemplified mineral powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like. As for the liquid carrier or diluent, there may be exemplified alcohols (e.g. methanol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methylethylketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene-oxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates, quaternary ammonium salts and the like. But, the surface active agent is not of course limited to these compounds. If necessary, gelatin, casein, sodium alginate, starch, agar, polyvinyl alcohol or the like may be used as an auxiliary agent.

In the herbicidal composition of this invention, the content of the N-benzylphenylacetamide derivative (I) may be usually from 0.05 to 95% by weight, preferably from 1 to 50% by weight.

Practical ebodiments of the herbicidal composition according to the invention are illustratively shown in the following examples wherein part(s) and % are by weight.

Preparation Example 1

Twenty-five parts of Compound No. 1, 2.5 parts of a dodecylbenzenesulfonate, 2.5 parts of a ligninsulfonate and 70 parts of diatomaceous earth are well mixed while being powdered to obtain a wettable powder.

Preparation Example 2

Fifteen parts of Compound No. 4, 10 parts of emulsifier ("Sorpol SM-100" manufactured by Toho Chemical Co., Ltd.) and 75 parts of xylene are well mixed to obtain an emulsifiable concentrate.

Preparation Example 3

Five parts of Compound No. 10, 1 part of white carbon, 5 parts of a ligninsulfonate and 89 parts of clay are well mixed while being powdered. The mixture is then kneaded with water, granulated and dried to obtain a granule.

Preparation Example 4

One part of Compound No. 31, 1 part of isopropyl phosphate, 68 parts of clay and 30 parts of talc are well mixed while being powdered to obtain a dust.

Preparation Example 5

Fourty parts of bentonite, 5 parts of a ligninsulfonate and 55 parts of clay are well mixed while being powdered. The mixture is then well kneaded with water, granulated and dried to obtain a granule containing no active ingredient. Ninety-five parts of the thus obtained granule are then impregnated with 5 parts of Compound No. 1 dissolved in acetone. Subsequent removal of acetone gives a granule.

Preparation Example 6

Ninety-five parts of bentonite of 16-48 mesh is impregnated with 5 parts of Compound No. 6 dissolved in acetone. Subsequent removal of acetone gives a granule.

Preparation Example 7

Fifty parts of Compound No. 33, 2.5 parts of a dodecylbenzenesulfonate, 2.5 parts of a ligninsulfonate and 45 parts of diatomaceous earth are well mixed while being powdered to obtain a wettable powder.

Preparation Example 8

Twenty parts of Compound No. 50, 10 parts of emulsifier ("Sormol SM-100" manufactured by Toho Chemical Co., Ltd.) and 70 parts of dimethylsulfoxide are well mixed to obtain an emulsifiable concentrate.

The N-benzylphenylacetamide derivative (I) may be used together with other herbicides to improve their activity as herbicides, and in some cases, to produce a synergistic effect. As the herbicides to be mixed with, there may be given phenoxy series herbicides such as 2,4-dichlorophenoxyacetic acid, 2-methyl-4-chlorophenoxybutyric acid and 2-methyl-4-chlorophenoxyacetic acid (including esters and salts thereof); diphenyl ether series herbicides such as 2,4-dichlorophenyl-4'-nitrophenyl ether, 2,4,6-trichlorophenyl-4'-nitrophenyl ether, 2-chloro-4-trifluoromethylphenyl-3'-ethoxy-4'-nitrophenyl ether, 2,4-dichlorophenyl-4'-nitro-3'-methoxyphenyl ether and 2,4-dichlorophenyl-3'-methoxycarbonyl-4'-nitrophenyl ether; triazine series herbicides such as 2-chloro-4,6-bisethylamino-1,3,5-triazine, 2-chloro-4-ethylamino-6-isopropylamino-1,3,5-triazine, 2-methylthio-4,6-bisethylamino-1,3,5-triazine, 2-methylthio-4,6-bisisopropylamino-1,3,5-triazine and 4-amino-6-t-butyl-3-methylthio-1,2,4-triazin-5-one; urea series herbicides such as 3-(3,4-dichlorophenyl)-1,1-dimethylurea, 3-(3,4-dichlorophenyl)-1-methoxy-1-methylurea and 1-(2,2-dimethylbenzyl)-3-p-tolylurea; carbamate series herbicides such as isopropyl-N-(3-chlorophenyl)carbamate and methyl-N-(3,4-dichlorophenyl)carbamate; thiolcarbamate series herbicides such as S-(4-chlorobenzyl)-N,N-diethylthiolcarbamate, S-ethyl-N,N-hexamethylenethiolcarbamate and S-ethyl-N,N'-diisobutylthiolcarbamate; acid anilide series herbicides such as 3,4-dichloropropionanilide, N-methoxymethyl-2,6-diethyl-α-chloroacetanilide, 2-chloro-2',6'-diethyl-N-butoxymethylacetanilide, 2-chloro-2',6'-diethyl-N-(n-propoxyethyl)acetanilide and N-chloroacetyl-N-(2,6-diethylphenyl)glycine ethyl ester; uracil series herbicides such as 5-bromo-3-sec-butyl-6-methyluracil and 3-cyclohexyl-5,6-trimethyleneuracil; pyridinium chloride series herbicides such as 1,1'-dimethyl-4,4-bispyridinium chloride; phosphorus series herbicides such as N,N-bis(phosphonomethyl)glycine, O-ethyl-O-(2-nitro-5-methylphenyl)-N-sec-butylphosphoroamidothioate, S-(2-methyl-1-piperidylcarbonylmethyl) O,O-di-n-propyldithiophosphate and S-(2-methyl-1-piperidylcarbonylmethyl) O,O-diphenyldithiophosphate; toluidine series herbicides such as α,α,α-trifluoro-2,6-dinitro-N,N-dipropyl-p-toluidine; 5-tert-butyl-3-(2,4-dichloro-5-isopropoxyphenyl)-1,3,4-oxadiazolin-2-one; 3-isopropyl-1H-2,1,3-benzothiadiazin-(4)-3H-one-2,2-dioxide; α-(β-naphthoxy)propionanilide; 4-(2,4-dichlorobenzoyl)-1,3-dimethylpyrazol-5-yl-p-toluenesulfonate; 4'-phenylsulfonyl-1,1,1-trifluorosulfono-O-toluidide and the like. But, the herbicides are not limited to these examples.

The herbicides of the invention may be applied together with insecticides, nematocides, fungicides, plant growth regulators, fertilizers, etc.

When the N-benzylphenylacetamide derivative (I) is used as a herbicide, it may be applied before or aftergermination of weeds in an amount within a wide range. The amount may be usually from about 10 grams to 1 kilogram per 10 ares, preferably from about 25 grams to 500 grams per 10 ares.

Some test examples which show the herbicidal activity of the N-benzylphenylacetamide derivatives (I) are shown in the following Examples wherein % is by weight.

EXAMPLE I

Seeds of large carbgrass (Digitaria sanguinalis), seeds of common lambsquarters (Chenopodium album), tubers of purple nutsedge (Cyperus rotundus), seeds of soybean and seeds of cotton were sowed or planted in a 10 cm flower pot and covered with soil. Separately, a required amount of each test compound was formulated into an emulsifiable concentrate and diluted with water. The diluted solution was applied to the soil by means of a hand sprayer, and the thus treated soil was mixed and kept to the depth of 2 cm from the soil surface. Cultivation was carried out in a greenhouse, and the herbicidal activity and phytotoxicity of the test compound were checked 20 days after the application. The test results are shown in Table 2. The herbicidal activity was evaluated in figures ranging from 0 to 5. The phytotoxicity to the crop plants was also indicated on the same standard as that of the herbicidal activity.

| FIGS. | Percentage of growth inhibition (%) |
|---|---|
| 0 | 0–9 |
| 1 | 10–29 |
| 2 | 30–49 |
| 3 | 50–69 |
| 4 | 70–89 |
| 5 | 90–100 |

TABLE 2

| Compound No. | Dosage (weight) of active ingredient, g/are | Herbicidal activity | | | Phytotoxicity | |
|---|---|---|---|---|---|---|
| | | Large crabgrass | Common lambsquarters | Purple nutsedge | Soybean | Cotton |
| 1 | 80 | 5 | 4 | 5 | 0 | 0 |
| | 40 | 5 | 4 | 5 | 0 | 0 |
| 2 | 80 | 5 | 4 | 5 | 0 | 0 |
| | 40 | 4 | 4 | 5 | 0 | 0 |
| 4 | 40 | 5 | 5 | 5 | 0 | 0 |
| | 20 | 5 | 4 | 5 | 0 | 0 |
| 5 | 80 | 4 | 5 | 5 | 0 | 0 |
| | 40 | 4 | 4 | 5 | 0 | 0 |
| 6 | 40 | 5 | 4 | 5 | 0 | 0 |
| | 20 | 5 | 4 | 5 | 0 | 0 |
| 9 | 40 | 5 | 5 | 5 | 0 | 0 |
| | 20 | 5 | 4 | 5 | 0 | 0 |
| 11 | 40 | 5 | 4 | 5 | 0 | 0 |
| | 20 | 5 | 4 | 5 | 0 | 0 |
| 12 | 80 | 5 | 4 | 5 | 0 | 0 |
| | 40 | 4 | 4 | 5 | 0 | 0 |
| 13 | 80 | 5 | 4 | 5 | 0 | 0 |
| | 40 | 5 | 4 | 5 | 0 | 0 |
| 17 | 80 | 5 | 4 | 5 | 0 | 0 |
| | 40 | 5 | 4 | 5 | 0 | 0 |
| 18 | 80 | 5 | 5 | 5 | 0 | 0 |
| | 40 | 5 | 4 | 5 | 0 | 0 |
| 24 | 160 | 5 | 4 | 5 | 0 | 0 |
| | 80 | 4 | 4 | 5 | 0 | 0 |
| 30 | 40 | 5 | 5 | 5 | 0 | 0 |
| | 20 | 5 | 4 | 5 | 0 | 0 |
| 31 | 40 | 5 | 5 | 5 | 0 | 0 |

TABLE 2-continued

| Compound No. | Dosage (weight) of active ingredient, g/are | Herbicidal activity | | | Phytotoxicity | |
|---|---|---|---|---|---|---|
| | | Large crab-grass | Common lambs-quarters | Purple nutsedge | Soy-bean | Cotton |
| | 20 | 5 | 5 | 5 | 0 | 0 |
| 32 | 40 | 5 | 5 | 5 | 0 | 0 |
| | 20 | 5 | 5 | 5 | 0 | 0 |
| 33 | 40 | 5 | 5 | 5 | 0 | 0 |
| | 20 | 5 | 5 | 5 | 0 | 0 |
| 34 | 40 | 5 | 5 | 5 | 0 | 0 |
| | 20 | 5 | 5 | 5 | 0 | 0 |
| 35 | 40 | 5 | 5 | 5 | 0 | 0 |
| | 20 | 5 | 4 | 5 | 0 | 0 |
| 36 | 40 | 5 | 5 | 5 | 0 | 0 |
| | 20 | 4 | 4 | 5 | 0 | 0 |
| 37 | 40 | 5 | 5 | 5 | 0 | 0 |
| | 20 | 5 | 5 | 5 | 0 | 0 |
| 38 | 40 | 5 | 5 | 5 | 0 | 0 |
| | 20 | 4 | 4 | 5 | 0 | 0 |
| 39 | 40 | 5 | 5 | 5 | 0 | 0 |
| | 20 | 4 | 4 | 5 | 0 | 0 |
| 40 | 40 | 5 | 5 | 5 | 0 | 0 |
| | 20 | 5 | 4 | 5 | 0 | 0 |
| 41 | 40 | 5 | 5 | 5 | 0 | 0 |
| | 20 | 4 | 5 | 5 | 0 | 0 |
| 42 | 40 | 5 | 5 | 5 | 0 | 0 |
| | 20 | 4 | 4 | 4 | 0 | 0 |
| 43 | 40 | 5 | 5 | 5 | 0 | 0 |
| | 20 | 5 | 5 | 4 | 0 | 0 |
| 44 | 40 | 5 | 5 | 5 | 0 | 0 |
| | 20 | 5 | 5 | 5 | 0 | 0 |
| 45 | 40 | 5 | 5 | 5 | 0 | 0 |
| | 20 | 4 | 5 | 4 | 0 | 0 |
| 46 | 40 | 5 | 5 | 5 | 0 | 0 |
| | 20 | 5 | 5 | 5 | 0 | 0 |
| 47 | 40 | 5 | 5 | 5 | 0 | 0 |
| | 20 | 5 | 5 | 5 | 0 | 0 |
| 48 | 40 | 5 | 5 | 5 | 0 | 0 |
| | 20 | 4 | 5 | 5 | 0 | 0 |
| 49 | 40 | 5 | 5 | 5 | 0 | 0 |
| | 20 | 5 | 5 | 5 | 0 | 0 |
| 50 | 40 | 5 | 5 | 5 | 0 | 0 |
| | 20 | 5 | 5 | 5 | 0 | 0 |
| 51 | 40 | 5 | 5 | 5 | 0 | 0 |
| | 20 | 5 | 5 | 5 | 0 | 0 |
| 52 | 40 | 5 | 5 | 5 | 0 | 0 |
| | 20 | 5 | 5 | 5 | 0 | 0 |
| 53 | 40 | 5 | 5 | 5 | 0 | 0 |
| | 20 | 4 | 4 | 5 | 0 | 0 |
| 54 | 40 | 5 | 5 | 5 | 0 | 0 |
| | 20 | 5 | 5 | 5 | 0 | 0 |
| 55 | 40 | 5 | 5 | 5 | 0 | 0 |
| | 20 | 4 | 5 | 5 | 0 | 0 |
| 56 | 40 | 5 | 5 | 5 | 0 | 0 |
| | 20 | 5 | 4 | 5 | 0 | 0 |
| 57 | 40 | 5 | 5 | 5 | 0 | 0 |
| | 20 | 4 | 4 | 4 | 0 | 0 |
| 58 | 40 | 5 | 5 | 5 | 0 | 0 |
| | 20 | 5 | 5 | 5 | 0 | 0 |
| 59 | 40 | 5 | 5 | 5 | 0 | 0 |
| | 20 | 5 | 5 | 5 | 0 | 0 |
| 60 | 40 | 5 | 5 | 5 | 0 | 0 |
| | 20 | 4 | 5 | 4 | 0 | 0 |
| A*[1] | 80 | 3 | 3 | 0 | 3 | 2 |
| | 40 | 2 | 1 | 0 | 2 | 1 |

Note:
*[1]Compound disclosed in U.S. Pat. No. 3,498,781:

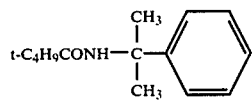

EXAMPLE II

A Wagner's pot of 14 cm in diameter was filled with 1.5 kg of paddy field soil and added with water to make a paddy field condition. Rice seedlings of 3-leaf growth stage were transplanted in the pot, and seeds of barnyard grass (*Echinochloa crus-galli*) and *Scirpus Hotarui*, and buds of slender spikerush (*Eleocharis acicularis*), which tided over the winter, were further sowed or planted therein. A required amount of each test compound was applied to the soil under a flooded condition. Twenty-five days after the application, the herbicidal activity and phytotoxicity of the test compound were checked on the plants as sowed or planted. The results are shown in Table 3.

As to the application, a wettable powder containing a required amount of the test compound was diluted with water and applied in a proportion of 15 ml/pot by means of a pipette. The herbicidal activity was evaluated according to the same criteria as in Example I.

With regard to the evaluation of phytotoxicity, the three factors (i.e. height of plant, number of tillers and total weight (dry weight)) were each checked, and a ratio of the treated plot to the untreated plot was calculated for each factor. The phytotoxicity was evaluated based on the lowest value in the three factors, which was classified into the following grades ranging from 0 to 5.

| Grade | Ratio of the untreated plot (%) |
|---|---|
| 0 | 100 |
| 1 | 90–99 |
| 2 | 80–89 |
| 3 | 60–79 |
| 4 | 40–59 |
| 5 | 0–39 |

TABLE 3

| Compound No. | Dosage (weight of active ingredient, g/are) | Herbicidal activity | | | Phytotoxicity |
|---|---|---|---|---|---|
| | | Barnyard grass | Scirpus Hotarui | Slender spikerush | Rice plant |
| 1 | 20 | 5 | 5 | 5 | 0 |
| | 10 | 5 | 5 | 5 | 0 |
| 2 | 20 | 5 | 5 | 5 | 0 |
| | 10 | 5 | 5 | 5 | 0 |
| 3 | 40 | 5 | 5 | 5 | 0 |
| | 20 | 5 | 4 | 5 | 0 |
| 4 | 20 | 5 | 5 | 5 | 0 |
| | 10 | 5 | 5 | 5 | 0 |
| 5 | 20 | 5 | 5 | 5 | 0 |
| | 10 | 5 | 5 | 5 | 0 |
| 6 | 20 | 5 | 5 | 5 | 0 |
| | 10 | 5 | 5 | 5 | 0 |
| 7 | 20 | 5 | 4 | 5 | 0 |
| | 10 | 5 | 4 | 5 | 0 |
| 8 | 80 | 4 | 4 | 5 | 0 |
| | 40 | 4 | 4 | 4 | 0 |
| 9 | 20 | 5 | 5 | 5 | 0 |
| | 10 | 5 | 5 | 5 | 0 |
| 10 | 20 | 5 | 5 | 5 | 0 |
| | 10 | 5 | 4 | 5 | 0 |
| 11 | 20 | 5 | 5 | 5 | 0 |
| | 10 | 5 | 5 | 5 | 0 |
| 12 | 20 | 5 | 5 | 5 | 0 |
| | 10 | 5 | 5 | 5 | 0 |
| 13 | 40 | 5 | 5 | 5 | 0 |
| | 20 | 5 | 5 | 5 | 0 |
| 14 | 20 | 5 | 5 | 5 | 0 |
| | 10 | 4 | 4 | 4 | 0 |
| 15 | 20 | 5 | 5 | 4 | 0 |
| | 10 | 5 | 5 | 4 | 0 |
| 16 | 80 | 4 | 4 | 4 | 0 |
| | 40 | 4 | 4 | 4 | 0 |
| 17 | 20 | 5 | 5 | 5 | 0 |
| | 10 | 5 | 5 | 5 | 0 |
| 18 | 20 | 5 | 5 | 5 | 0 |
| | 10 | 5 | 5 | 4 | 0 |

TABLE 3-continued

| Compound No. | Dosage (weight of active ingredient, g/are) | Herbicidal activity Barnyard grass | Scirpus Hotarui | Slender spikerush | Phytotoxicity Rice plant |
|---|---|---|---|---|---|
| 19 | 40 | 5 | 5 | 5 | 0 |
|  | 20 | 5 | 4 | 5 | 0 |
| 20 | 80 | 4 | 4 | 5 | 0 |
|  | 40 | 4 | 4 | 4 | 0 |
| 21 | 80 | 4 | 4 | 4 | 0 |
|  | 40 | 4 | 4 | 4 | 0 |
| 22 | 80 | 5 | 4 | 4 | 0 |
|  | 40 | 4 | 4 | 4 | 0 |
| 23 | 80 | 4 | 4 | 5 | 0 |
|  | 40 | 4 | 4 | 4 | 0 |
| 24 | 20 | 5 | 5 | 5 | 0 |
|  | 10 | 5 | 5 | 5 | 0 |
| 25 | 80 | 5 | 4 | 5 | 0 |
|  | 40 | 4 | 4 | 5 | 0 |
| 26 | 20 | 5 | 5 | 5 | 0 |
|  | 10 | 5 | 4 | 5 | 0 |
| 27 | 80 | 5 | 5 | 4 | 0 |
|  | 40 | 5 | 4 | 4 | 0 |
| 28 | 80 | 4 | 4 | 5 | 0 |
|  | 40 | 4 | 4 | 4 | 0 |
| 29 | 80 | 4 | 4 | 4 | 0 |
|  | 40 | 4 | 4 | 4 | 0 |
| 30 | 20 | 5 | 5 | 5 | 0 |
|  | 10 | 5 | 5 | 5 | 0 |
| 31 | 20 | 5 | 5 | 5 | 0 |
|  | 10 | 5 | 5 | 5 | 0 |
| 32 | 20 | 5 | 5 | 5 | 0 |
|  | 10 | 5 | 5 | 5 | 0 |
| 33 | 20 | 5 | 5 | 5 | 0 |
|  | 10 | 5 | 5 | 5 | 0 |
| 34 | 20 | 5 | 5 | 5 | 0 |
|  | 10 | 5 | 5 | 5 | 0 |
| 35 | 20 | 5 | 5 | 5 | 0 |
|  | 10 | 5 | 5 | 5 | 0 |
| 36 | 20 | 5 | 5 | 5 | 0 |
|  | 10 | 4 | 5 | 5 | 0 |
| 37 | 20 | 5 | 5 | 5 | 0 |
|  | 10 | 4 | 5 | 4 | 0 |
| 38 | 20 | 5 | 5 | 5 | 0 |
|  | 10 | 5 | 4 | 5 | 0 |
| 39 | 20 | 5 | 5 | 5 | 0 |
|  | 10 | 4 | 4 | 4 | 0 |
| 40 | 20 | 5 | 5 | 5 | 0 |
|  | 10 | 4 | 4 | 5 | 0 |
| 41 | 20 | 5 | 5 | 5 | 0 |
|  | 10 | 4 | 5 | 5 | 0 |
| 42 | 20 | 5 | 5 | 5 | 0 |
|  | 10 | 5 | 5 | 5 | 0 |
| 43 | 20 | 5 | 5 | 5 | 0 |
|  | 10 | 5 | 5 | 5 | 0 |
| 44 | 20 | 5 | 5 | 5 | 0 |
|  | 10 | 4 | 5 | 5 | 0 |
| 45 | 20 | 5 | 5 | 5 | 0 |
|  | 10 | 5 | 5 | 4 | 0 |
| 46 | 20 | 5 | 5 | 5 | 0 |
|  | 10 | 5 | 4 | 4 | 0 |
| 47 | 20 | 5 | 5 | 5 | 0 |
|  | 10 | 5 | 5 | 5 | 0 |
| 48 | 20 | 5 | 5 | 5 | 0 |
|  | 10 | 4 | 4 | 5 | 0 |
| 49 | 20 | 5 | 5 | 5 | 0 |
|  | 10 | 4 | 4 | 5 | 0 |
| 50 | 20 | 5 | 5 | 5 | 0 |
|  | 10 | 5 | 5 | 5 | 0 |
| 51 | 20 | 5 | 5 | 5 | 0 |
|  | 10 | 5 | 5 | 5 | 0 |
| 52 | 20 | 5 | 5 | 5 | 0 |
|  | 10 | 5 | 5 | 5 | 0 |
| 53 | 20 | 5 | 5 | 5 | 0 |
|  | 10 | 4 | 4 | 4 | 0 |
| 54 | 24 | 5 | 5 | 5 | 0 |
|  | 10 | 5 | 5 | 5 | 0 |
| 55 | 20 | 5 | 5 | 5 | 0 |
|  | 10 | 5 | 5 | 5 | 0 |
| 56 | 20 | 5 | 5 | 5 | 0 |
|  | 10 | 4 | 5 | 5 | 0 |
| 57 | 20 | 5 | 5 | 5 | 0 |
| 58 | 10 | 5 | 4 | 5 | 0 |
|  | 20 | 5 | 5 | 5 | 0 |
| 59 | 10 | 5 | 5 | 5 | 0 |
|  | 20 | 5 | 5 | 5 | 0 |
| 60 | 10 | 5 | 5 | 5 | 0 |
|  | 20 | 5 | 5 | 5 | 0 |
|  | 10 | 4 | 4 | 5 | 0 |
| Untreated | — | 0 | 0 | 0 | 0 |

What is claimed is:

1. A compound of the formula:

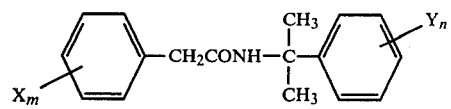

wherein X and Y, which may be same or different, are each a $C_1$–$C_3$ alkyl group, a halogen atom, a trifluoromethyl group, a nitro group or a $C_1$–$C_3$ alkoxy group, m is an integer of 0 to 3 and n is an integer of 1 or 2.

2. The compound according to claim 1, wherein X is a methyl group, a fluorine atom, a chlorine atom, a trifluoromethyl group or a methoxy group, Y is a methyl group, a fluorine atom, a chlorine atom or a bromine atom or a methoxy group, m is an integer of 0 to 2 and n is an integer of 1 or 2.

3. The compound according to claim 1, wherein X is a methyl group, a fluorine atom, a chlorine atom or a methoxy group, m is an integer of 0 or 1, Y is a methyl group, a fluorine atom or a chlorine atom and n is an integer of 1, provided that when m or n is an integer of 1, X or Y is present at the m- or o-position.

4. A compound according to claim 1, namely N-(2-Methyl-α,α-dimethylbenzyl)-o-methylphenylacetamide.

5. A compound according to claim 1, namely N-(3-Chloro-α,α-dimethylbenzyl)-o-fluorophenylacetamide.

6. A compound according to claim 1, namely N-(3-Chloro-α,α-dimethylbenzyl)-o-chlorophenylacetamide.

7. A compound according to claim 1, namely N-(3-Methyl-α,α-dimethylbenzyl)-o-chlorophenylacetamide.

8. A compound according to claim 1, namely N-(2-Methyl-α,α-dimethylbenzyl)-m-chlorophenylacetamide.

9. A herbicidal composition which comprises as an active ingredient a herbicidally effective amount of the compound according to claim 1 and an inert carrier or diluent.

10. A method for controlling a weed which comprises applying a herbicidally effective amount of the compound according to claim 1 to the weed.

11. A method for controlling the growth of a weed which comprises applying a herbicidally effective amount of the herbicidal composition according to claim 9 to an area where the weed is growing or will grow.

12. A method for controlling the growth of a weed where crops selected from the group consisting of rice, soybean, cotton, corn, peanut, sugarbeet, sunflower, lettuce and cabbage are growing which comprises applying a herbicidally effective amount of the compound according to claim 1, 2 or 3 to the area where said crops are growing.

13. The method according to claim 12, wherein said crop is rice, soybean or cotton.

* * * * *